(12) United States Patent (10) Patent No.: US 8,965,091 B2
Popescu (45) Date of Patent: Feb. 24, 2015

(54) METHOD AND IMAGE-RECONSTRUCTION APPARATUS FOR RECONSTRUCTING IMAGE DATA

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 887 days.

(21) Appl. No.: 13/111,159

(22) Filed: May 19, 2011

(65) Prior Publication Data

US 2011/0293158 A1 Dec. 1, 2011

(30) Foreign Application Priority Data

May 25, 2010 (DE) .......................... 10 2010 029 281

(51) Int. Cl.
  *G06K 9/00* (2006.01)
  *A61B 6/00* (2006.01)
  *A61B 5/055* (2006.01)
  *A61B 6/03* (2006.01)
  *G06T 11/00* (2006.01)
  *A61B 5/00* (2006.01)

(52) U.S. Cl.
  CPC .............. *A61B 6/5205* (2013.01); *A61B 5/055* (2013.01); *A61B 6/032* (2013.01); *A61B 6/037* (2013.01); *G06T 11/006* (2013.01); *G06T 2211/424* (2013.01); *A61B 5/7232* (2013.01)
  USPC ............................ 382/131; 382/266; 382/275

(58) Field of Classification Search
  USPC ................................ 382/131, 266, 274, 275
  See application file for complete search history.

(56) References Cited

U.S. PATENT DOCUMENTS

| | | | |
|---|---|---|---|
| 6,865,494 B2* | 3/2005 | Duensing et al. | 702/38 |
| 7,864,999 B2* | 1/2011 | Chang et al. | 382/128 |
| 2006/0062486 A1* | 3/2006 | Lee et al. | 382/276 |
| 2006/0215891 A1* | 9/2006 | Fessler et al. | 382/128 |
| 2007/0110290 A1 | 5/2007 | Chang | |
| 2009/0161932 A1 | 6/2009 | Chen | |
| 2010/0054394 A1 | 3/2010 | Bouman et al. | |

OTHER PUBLICATIONS

Block et al. "Undersampled Radial MRI with Multiple Coils. Iterative Image Reconstruction Using a Total Variation Constraint", Magnetic Resonance in Medicine 57:1086-1098 (2007).*
Guang-Hong Chen et al., Prior Image Constrained Compressed Sensing (PICCS), Proc. of SPIE vol. 6856 685618-14, published 2008, 14 pages.*
NPL—Michael Lustig et al., "Sparse MRI The Application of Compressed Sensing", Magnetic Resonance in Medicine 58:1182-1195 (2007).*
Jeffrey Fessler, Iterative Methods for Image Reconstruction, University of Michigan, 2008, 79 pages.*
German Priority application 10 2010 029 281.8, filed on May 25, 2010 (not yet published).

(Continued)

*Primary Examiner* — Wesley Tucker
(74) *Attorney, Agent, or Firm* — Harness, Dickey & Pierce

(57) ABSTRACT

A method and an image-reconstruction apparatus are disclosed for reconstructing image data on the basis of measurement data from an imaging system. In at least one embodiment of the process, initial image data, initially reconstructed from the measurement data, is optimized in an iterative optimization method utilizing a substantially edge-maintaining noise regularization term and an additional sparsity regularization term.

23 Claims, 3 Drawing Sheets

(56) References Cited

OTHER PUBLICATIONS

Michael Lustig, David Donoho and John M. Pauly, Sparse MRI: The Application of Compressed Sensing for Rapid MR Imaging, University of Stanford; Others, 2007.

Stephen Boyd and Lieven Vandenberghe, Convex Optimization, Cambridge University Press, 2004; Others.

Jeromin, O. et al: "Optimal sampling geometries for TV-Norm reconstruction of fMRI data", Proceedings of the 42nd Asilomar Conference on Signals, Systems and Computers, 2008, S. 1397-1401; Others; 2008.

Zheng, K. et al: "Parallel image reconstruction by adaptively weighted H optimization" Proceedings of the IEEE International Conference on Control and Automation, 2009, p. 1796-1800; Others; 2009.

Block, K.T. et al: "Undersampled radial MRI with multiple coils. Iterative Image Reconstruction Using a Total Variation Constraint", Magnetic Resonance in medicine, vol. 57, 2007, p. 1086-1098; Others; 2007.

Jeffrey A. Fessler: "Statistical Methods for Image Reconstruction", Johns Hopkins University, "Short" Course, May 11, 2007; Others; 2007.

* cited by examiner

METHOD AND IMAGE-RECONSTRUCTION APPARATUS FOR RECONSTRUCTING IMAGE DATA

PRIORITY STATEMENT

The present application hereby claims priority under 35 U.S.C. §119 on German patent application number DE 10 2010 029 281.8 filed May 25, 2010, the entire contents of which are hereby incorporated herein by reference.

FIELD

At least one embodiment of the invention generally relates to a method and/or to an image-reconstruction apparatus for reconstructing image data on the basis of measurement data from an imaging system. The imaging system may be a medical-technical system such as e.g. a magnetic resonance system, an X-ray computed tomography system, a positron emission tomography (PET) system, a single photon emission computed tomography (SPECT) system or the like. Depending on the imaging system used, the measurement data accordingly is raw magnetic-resonance data, i.e. spatially encoded magnetic-resonance signals, X-ray projection data records, PET or SPECT data records, etc. Moreover, the invention relates to a method for generating image data of the interior of an object using such a reconstruction method.

BACKGROUND

In principle, these days there are two classes of methods for reconstructing image data.

The first method class relates to analytic methods such as e.g. the so-called filtered back projection (FBP) method in the case of computed tomography projection data or a two-dimensional inverse Fourier transform in the case of raw magnetic-resonance data. Here, these respectively are single-step image calculation procedures, which are based on idealized mathematical system models that permit the derivation of analytic inverse solutions of the equation to be calculated. By way of example, if a record X of unknown object properties (e.g. local tissue properties that are ultimately represented by the image to be reconstructed) is assumed, these object properties are imaged on a record Y of measurement values by the system transfer function A (the so-called transfer function) of the imaging system:

$$Y = A \cdot X. \tag{1}$$

Here, the data records X and Y are written in the form of matrices. In such an idealized mathematical system model, both the transfer function A and the inverse $A^{-1}$ thereof are known, and so, conversely, the record X of the unknown object properties, i.e. the image to be reconstructed, can be calculated as per $$X = A^{-1} \cdot Y \tag{2}$$

from the obtained measurement values Y.

These methods are generally very time-saving reconstruction methods. However, the problem of these methods consists of the fact that in this case the non-ideal properties of real imaging systems are not taken into account. By way of example, in a real magnetic resonance system this non-ideal property can be seen in the always present Gaussian noise, in the inhomogeneous magnetic fields, in defects in respect of the recording sensitivity, radiofrequency inhomogeneities, etc. In the case of CT scanners, such real, non-ideal properties that should be taken into account during the reconstruction lead to e.g. quantum noise, scattered X-ray radiation, beam hardening effects, etc.

It is for this reason that relatively time-intensive, recursive methods are used in a second group of reconstruction methods, which recursive methods avoid the requirement of developing an analytic solution in advance.

Such an iterative reconstruction method usually begins with an initial estimate of initial image data $X_0$. Image data established with a classical analytic method as per equation (2) may for example be used in the process. Using this initial image data $X_0$ as a starting point, the image data is then successively improved iteratively as per the following equation:

$$X_{k+1} = X_k - \Delta X_k \tag{3}$$

That is to say, image correction data $\Delta X_k$ is calculated in each step k and used to generate updated, improved image data $X_{k+1}$ from the current image data $X_k$. The goal here is to minimize data mismatch between the real measurement values Y and the synthesized measurement values $Y_k$, which are respectively calculated in the current iteration step as per $$Y_k = A \cdot X_k \tag{4}$$

In order to calculate the image correction data $\Delta X_k$ in each iteration step, use can be made of various algorithms, as known to a person skilled in the art from the prior art, for example the gradient of the steepest descent, a conjugate gradient or other similar methods. By way of example, the image correction data $\Delta X_k$ may be calculated as per the equation $$\Delta X_k = \alpha \cdot \mathrm{grad}(f_z). \tag{5}$$

The parameter $\alpha$ describes a relaxation parameter, which controls the convergence speed. In this case, it may be an arbitrary value, preferably in the range between 0 and 1, e.g. a value of 0.7. $f_z$ is a target function, such as e.g.

$$f_z = \|A \cdot X - Y\|_2. \tag{6}$$

Here, the notation $\|Z\|_2$ is used for the $L_2$ norm of Z.

The above-described method can also be expressed as a nonlinear mathematical optimization problem, restricted by boundary conditions, as per:

$$\min \|A \cdot X - Y\|_2, \text{with } X > 0. \tag{7}$$

That is to say, the target function $f_z$ as per equation (6) is minimized under the boundary condition that the values of the individual image pixels or voxels of the image data record X are all greater than 0.

Equations (6) and (7) hold true in the case of a so-called "least-squares minimization". However, in principle, it is also possible to use other target functions, as will still be outlined below. The respectively ideal target function depends, inter alia, on the imaging system used.

The main advantage of these iterative methods includes also allowing the use of transfer functions A for nonlinear and non-ideal measurement systems.

In order to improve the iterative methods further and to take improved account of the real measurement conditions, it is possible, within the optimization method, to take into account a statistical model for the noise adversely affecting the measurement results. To this end, a method is described in, for example, Jeffrey A. Fessler, Statistical Methods for Image Reconstruction, John Hopkins University: "Short" Course, May 11, 2007.

To this end, a so-called noise regularization term is inserted in e.g. the target function $f_z$ in the above-described optimization method, which noise regularization term is formulated mathematically such that relatively high image noise is suppressed. Optimization methods using noise regularization terms are described, for example, in US 2010/0054394 A1 and in K. Zheng and J. Zhang, "Parallel MR Image Reconstruction by Adaptively Weighted H∞ Optimization", Proceedings of the IEEE International Conference on Control and Automation, 2009, p. 1796-1800. The noise regularization term should preferably be constructed such that it is targeted to maintain the image contrast, more particularly edges and image sharpness, to the best possible extent within the optimization.

Additionally, for some time now there has been a novel reconstruction method, which is also known as a "compressed-sensing" method (CS method). This is a reconstruction method that can be used to generate quite good reconstructions from undersampled and/or compressed measurement data as well. The undersampled data is measurement data that was sampled below the Nyquist limit. It was found that under certain circumstances useful images can be generated from measurement data sampled under the Nyquist limit if there is random undersampling instead of coherent undersampling. By way of example, it is possible to record fewer projections, controlled in a random fashion, during each revolution of a computed tomography scanner. This leads to a reduction in the X-ray exposure of the patient. In the case of a magnetic-resonance system, it is possible, for example, for fewer lines to be sampled in an incoherent fashion in Fourier space, and so this can reduce the measurement time and, ultimately, the heating of the tissue by the radiofrequency load as well.

By way of example, a suitable reconstruction method is described in Michael Lustig et al., "Compressed Sensing for Rapid MR Imaging", University of Stanford. The reconstruction of such undersampled measurement data is also carried out using an iterative method, with, however, the generation of an image with great "sparsity" being forced, which is why the method is also referred to as "sparsity enforcing reconstruction" (SER). In the process, an attempt is made to reconstruct the image from the undersampled data such that it does not have too many details. Depending on the posed question of the examination, this often makes sense. Thus, for example, in the case of angiographic recordings, the aim generally is only to visualize the contrast-agent-filled blood vessels to the best possible extent, with the details around the blood vessels being of little interest and rather bothersome. In images with too much image noise, even e.g. the noise forms details, but these offer no information for a subsequent diagnosis and are rather bothersome. Such cases also call for an image with relatively great sparsity.

By way of example, a sparsity enforcing reconstruction may be implemented by virtue of the fact that a so-called "sparsity regularization term" is utilized in the aforementioned optimization method, for example within the target function. Various options for forming sparsity regularization terms will still be mentioned below. By way of example, US 2009/0161932 A1 outlines a method in which two sparsity regularization terms are utilized side by side in the target function. US 2007/0110290 A1 describes a method in which use is made of a weighted sum of various sparsity regularization terms.

SUMMARY

The inventor discovered that a basic problem of CS resides in the fact that the general image noise is increased. By way of example, in the case of magnetic-resonance systems, this is due to the fact that a reduction in the measurement time is automatically connected with increased image noise. Likewise, a reduction of the overall radiation dose in X-ray computed tomography scanners, and in similar tomographic methods such as SPECT or PET, necessarily increases the image noise as a result of the known effect of the mentioned "photon starvation".

By suitably selecting a sparsity regularization term, for example by using the variation (total variation), it is however possible to reduce the noise slightly. An example for this is described in the article "Optimal sampling geometries for TV-Norm Reconstruction of fMRI data" by Oliver M. Jeromin et al., in Proceedings of the 42nd Asilomar Conference on Signals, Systems, and Computers, 2008, p. 1397-1401. Herein, it is proposed to introduce a further regularization term on the basis of the total variation in addition to a first sparsity regularization term. An appropriate regularization term is also described in the method according to K. T. Block et al., "Undersampled Radial MRI with Multiple Coils. Iterative Image Reconstruction Using a Total Variation Constraint", Magn. Res. Med., Vol. 57, 2007, p. 1086-1098.

The inventor further discovered, however, that inexpediently this type of noise reduction is connected with a loss of image sharpness because a sparsity regularization term does not allow simultaneous maximization of the image sparsity and maintaining of the edges in the image to the best possible extent. Consequently, there always has to be a trade-off between noise reduction and acceptable image sharpness.

At least one embodiment of the present invention is directed to an improved reconstruction method and an image-reconstruction apparatus, which, compared to previous SER methods, allow an increased image sharpness to be obtained in the reconstructed image data when using undersampled or correspondingly compressed measurement data.

At least one embodiment is directed to a method and at least one embodiment is directed to an image-reconstruction apparatus.

In the reconstruction method according to at least one embodiment of the invention, initial image data is initially reconstructed from the measurement data and then optimized in an iterative optimization method utilizing a substantially edge-maintaining noise regularization term and an additional, i.e. separate, sparsity regularization term, which is independent of the noise regularization term. Here, a "substantially edge-maintaining" noise regularization term should be understood to mean a noise regularization term that ensures such noise reduction that the edges in the image are maintained to the greatest possible extent and consequently that there is no loss of image sharpness, or only a very small loss thereof, unlike e.g. a regularization term using total variation, which, although it can slightly reduce the noise as described above, can at best serve as a sparsity regularization term within the scope of at least one embodiment of the invention because it leads to a smoothing of the edges. Examples of edge-maintaining noise regularization will still be explained below.

Within the scope of comprehensive simulation methods, the inventor surprisingly discovered that, unlike previously, it is possible to use not only a noise regularization term or, alternatively, a sparsity regularization term within an iterative optimization method in order thereby to carry out a sparsity enforced reconstruction on undersampled data, but that the simultaneous use of two separate regularization terms achieves a synergistic effect, and thereby obtains image data with a high image sharpness, which has not been achieved by the previously known methods, can be generated from undersampled measurement data. Here, the noise regularization term and the sparsity regularization term are selected depending on the imaging system used, the type of measurement data, and possibly the goal for which the reconstructed image data should be used.

In the case of a method according to at least one embodiment of the invention for generating imaging data of the interior of an object by means of a medical-technical system, measurement data of the object of the examination is initially acquired with the aid of the imaging system, for example an MRI scanner, a CT scanner, a PET or a SPECT scanner of the imaging system, which measurement data represents image information of the relevant object. The image data is subsequently reconstructed from the obtained measurement data with the aid the aforementioned reconstruction method according to at least one embodiment of the invention.

In addition to a measurement-data interface for receiving measurement data obtained by way of an imaging system, an image-reconstruction apparatus according to at least one embodiment of the invention for reconstructing image data of an object requires a suitable reconstruction unit designed to reconstruct image data on the basis of the measurement data using an iterative reconstruction method, wherein initial image data, initially reconstructed from the measurement data, is optimized in an iterative optimization method utilizing a substantially edge-maintaining noise regularization term and an additional sparsity regularization term. Moreover, the image-reconstruction apparatus has an image-data interface for outputting the reconstructed image data.

By way of example, such a reconstruction unit can include an initial reconstruction unit and a subsequent optimization unit, wherein the initial reconstruction unit for example firstly reconstructs the initial image data from the measurement data using an analytic method and the subsequent optimization unit carries out the optimization on the basis of this initial image data.

Incidentally, the image-reconstruction unit itself can be part of an imaging system, i.e. it may for example be installed on a control and evaluation computer of the imaging system in a conventional fashion. However, in principle such an image-reconstruction apparatus may also be implemented in the form of another computer unit, or thereon, which other computer unit for example is connected to an imaging system over a network for receiving the data or can be supplied with measurement data in any other fashion.

In particular, the reconstruction unit (for example the initial reconstruction unit and the optimization unit) can be implemented in the form of software on a suitable computer with appropriate storage options. The measurement-data interface and the image-data interface can likewise be implemented purely in the form of software, provided all that is necessary is reception of the projection measurement data and/or output of the image data from respectively to other further measurement-data preprocessing units or image-data further processing units implemented on the same computer unit. However, in principle, these interfaces may also be implemented as combined hardware/software interfaces in order to implement an external input and output, for example with the aid of software components of specifically configured hardware interfaces. Here, output of the image data should not only be understood to mean an external output to a monitor, a printer or the like, but any output of the image data by the image-reconstruction apparatus, for example storing the image data in a storage medium for later viewing or further processing.

An advantage of a largely software-based implementation is that even previously used image-reconstruction apparatuses can easily be upgraded by a software update in order to operate in accordance with the invention. In this respect, the object is also achieved by a computer program product, which can be loaded directly into a storage medium of a programmable image-reconstruction apparatus, with program code sections to carry out all steps of the method according to at least one embodiment of the invention when the program is carried out in the image-reconstruction apparatus. Fortunately, the reconstruction method according to at least one embodiment of the invention is not connected with increased complexity over the known iterative reconstruction methods, but can easily be implemented on image-reconstruction apparatuses that are already in use.

Further advantageous refinements and developments of embodiments of the invention emerge from the further dependent claims and from the subsequent description. In the process, the image-reconstruction apparatus according to embodiments of the invention can also be developed in an analogous fashion to the dependent method claims.

As in the previously known iterative methods, respectively current image correction data is also established in the individual iteration steps of the method according to at least one embodiment of the invention using previously currently generated image data, which current image correction data is then used to calculate image data of a subsequent iteration stage. By way of example, in the first iteration stage, this is the initial image data, on the basis of which image correction data is then established, which—as illustrated above on the basis of equation (3) for example—can be used to generate updated image data. In the next stage, this updated image data is then utilized to calculate new image correction data, which is then used in turn to once again update the image data. The iterative method is finally aborted when a predefined convergence criterion has been reached, for example if the values in the image correction data are smaller than a certain $\epsilon$-value, which is therefore equivalent to the target function having converged to a sufficient extent within the optimization method. It is likewise possible to abort the iteration after a maximum number of iteration steps.

However, in the iterative method according to at least one embodiment of the invention, the current image correction data can be generated during each iteration utilizing the noise regularization term and the additional sparsity regularization term. In the process, the noise regularization term and the sparsity regularization term can, particularly preferably, simply be used as additional target function terms, i.e. as parts within a target function that should be optimized using the iterative method.

The target function and optionally further boundary conditions are preferably selected in the process such that they are convex functions that are certain to converge to an unambiguous minimum and do not have further local maxima or minima. There are special classes of mathematical optimization problems that have both a convex target function and convex boundary conditions and are known always to converge to an unambiguous minimum. Therefore, suitable target functions and boundary conditions can also be selected in the reconstruction method according to at least one embodiment of the invention when these classes are taken into account.

The noise regularization term and the sparsity regularization term are advantageously respectively weighted by a weighting factor during the optimization, for example within the target function. These weighting factors afford the possibility of setting the influence that the individual regularization terms respectively have on the optimization. By way of example, the weighting factor for the noise regularization term affords the possibility of varying the ratio between the noise and the spatial resolution, whereas the weighting factor for the sparsity regularization term controls the degree of the possible undersampling.

The weighting factors of the noise regularization term and the sparsity regularization term are particularly preferably selected such that the sum of the two weighting factors lies between 0 and 1, for example around 0.5.

The weighting factors can preferably be selected interactively by a user. As a result, the user of the imaging system or the reconstruction unit has the option of successively carrying out multiple reconstructions using various arbitrary weighting factors.

The measurement data is preferably undersampled at a specific undersampling rate. As an alternative to such direct undersampling, it is also possible to generate undersampled data by a retrospective compression of the measurement data, for example by dispensing with incoherent measurement data within the data record. Thus, the method is also suitable for use if the measurement data is connected to much image noise and it is expedient to process this measurement data using a sparsity enforced reconstruction method in order thus to obtain images with a high degree of sparsity, in which unnecessary image details, which in any case do not supply information, have been removed. Additionally, this affords the possibility of also storing measurement data in the form of compressed raw data with reduced storage space requirements.

Here, the undersampling rate should be understood to mean the degree of the undersampling in relation to full sampling at the Nyquist limit. That is to say, an undersampling rate of 1 means that there has been full sampling at the Nyquist limit, and an undersampling of 0.5 means that only 50% of the data was acquired compared to full sampling. In the field of the accelerated parallel imaging in MRI, use is also made of the term reduction factor or acceleration factor R, with R=2 meaning an undersampling of 0.5. That is to say the degree of undersampling is $1/R$. It is particularly preferable for the weighting factor of the sparsity regularization term to be selected as a function of the undersampling rate. Here, in a particularly preferred variant, it is possible for a summation value, which—as explained above—preferably lies between 0 and 1, to be prescribed for the weighting factors of the noise regularization term and the sparsity regularization term, and for the component of the weighting factor of the sparsity regularization term in the summation value then to be selected as a function of the undersampling rate. This allows an optimum selection of the weighting factors and hence of the influence of the "normal" noise regularization term and the sparsity regularization term.

As already explained above, current image correction data is preferably firstly established in each iteration step from the current image data utilizing the noise regularization term and the sparsity regularization term. In a first method variant, this takes place in one step and new updated image data for the next iteration step is then generated on the basis of the currently generated image data and the current image correction data, for example by a subtraction as is equation (3). That is to say, in this case the image is updated in a single stage whilst at the same time taking account of the noise regularization term and the sparsity regularization term.

In an alternative variant of at least one embodiment of the method, in an iteration step, current first image correction data is firstly established in a first stage using previously currently generated image data utilizing the noise regularization term or the sparsity regularization term. New current interim image data is then generated on the basis of this currently generated image data and the current first image correction data. Only then is current second image correction data established in a second stage of the iteration step using the current interim image correction data utilizing the sparsity regularization term or the noise regularization term (depending on which of these regularization terms was already utilized in the first stage). New current image data is then generated for the next iteration step on the basis of the current interim image correction data and the current second image correction data. Thus, in this method there is successive image updating, wherein the image correction data is updated in respect of one of the two regularization terms in the first stage and, in the second stage, there then is the update in respect of the other regularization term.

When the method according to at least one embodiment of the invention is applied, it is also possible to preprocess the measurement data as desired, as is also otherwise the case in the conventional reconstruction methods. By way of example, X-ray computed tomography measurement data can firstly be subjected to a beam-hardening correction. Any desired post-processing of the reconstructed image data is likewise possible.

BRIEF DESCRIPTION OF THE DRAWINGS

With the aid of example embodiments, the invention will once again be explained in more detail below with reference to the attached figures, in which.

DETAILED DESCRIPTION OF THE EXAMPLE EMBODIMENTS

Figure 1:
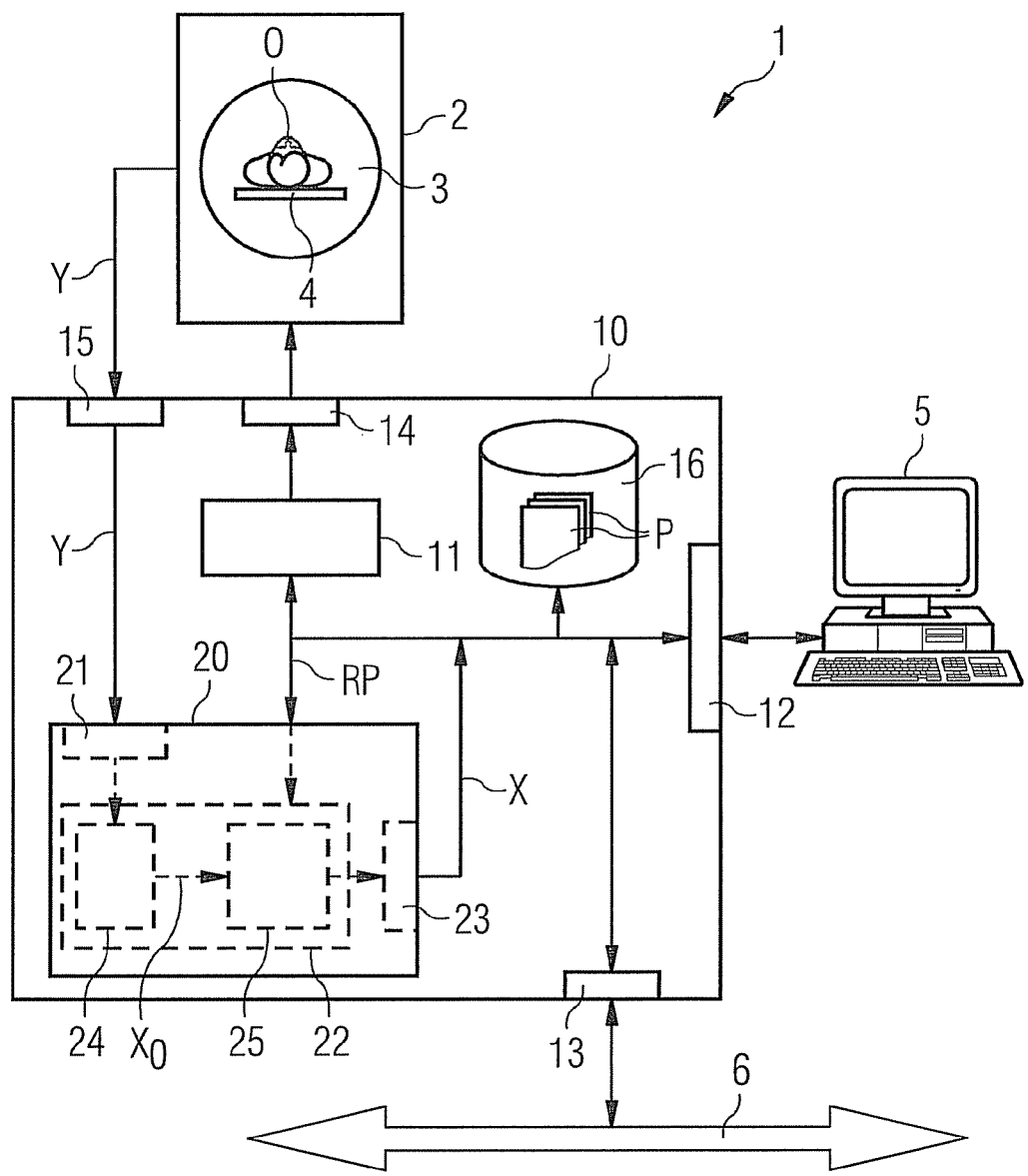
FIG. 1 shows a schematic illustration of an example embodiment of a medical-technical imaging system with an image-reconstruction apparatus.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 first of all schematically illustrates a medical-technical imaging system with an image-reconstruction apparatus 20, wherein this is an image-reconstruction apparatus 20 according to an embodiment of the invention, which—as will be detailed below—uses a noise regularization term and additionally a sparsity regularization term within an optimization method.

By way of example, the imaging system 1 may be a magnetic resonance system with a conventional MR scanner 2, in which a patient couch 4 is housed in an examination tunnel 3, with it being possible to position an examination object O, e.g. a patient or a subject, thereon. However, the MR system 1 is merely illustrated here as an example for other medical-technical imaging systems. By way of example, if this were a CT system, use would be made of a CT scanner instead of the MR scanner 2, in which CT scanner a detector system, with a detector and an X-ray source opposite said detector, circulates on a gantry that encircles an examination space. There, an examination object is likewise positioned on a patient couch within the gantry.

A control apparatus 10 actuates both the scanner 2 and the patient couch 4. This may be a conventional central control computer 10. The latter is equipped with a corresponding control interface 14 and a measurement control unit 11. This measurement control unit 11 actuates the scanner 2 as per a prescribed measurement protocol P for carrying out a measurement.

In this case, the control interface 14 is only illustrated as a block. However, it is obvious that this interface 14 generally includes a multiplicity of individual interfaces in the case of a medical-technical system. By way of example, in the case of a magnetic resonance device, the control interface 14 may comprise interfaces for actuating the gradient system, a radiofrequency transmission system for emitting the radiofrequency pulses, etc. In the case of a CT scanner, there would be a need for an interface for actuating the X-ray source and the motors in the gantry. Furthermore, this control interface 14 also comprises an interface for transmitting control signals to the patient couch.

The measurement data Y acquired by the scanner 2 is received by the control computer 10 via an image-data reception interface 15. This interface 15 may also consist of a plurality of partial interfaces. The measurement data Y is then transmitted to the image-reconstruction apparatus 20, which reconstructs the image data X therefrom, which image data is then for example displayed on a monitor of a terminal 5 in situ and/or stored on a storage medium 16 and/or transmitted to a data bus 6 via a network interface 13, by means of which the imaging system 1 is connected to other apparatuses within a network, in order, for example, to store measurement data or completely reconstructed image data on high-capacity mass storage media or to send said data to diagnostic stations or the like.

The entire imaging system 1 is actuated by an operator via the terminal 5, which is connected to the central control unit 10 via a terminal interface 12. This terminal 5 and a user interface implemented thereon for example enable the user to select a measurement protocol P from the storage medium 16, possibly adapt it, and ensure that the measurement control unit emits, via the control interface 14, appropriate control signals to the scanner 2 on the basis of this protocol such that the measurement can be carried out.

The measurement data Y acquired by the scanner 2 is transmitted to the image-reconstruction apparatus 20 via a measurement-data interface 21. Said data then reaches a reconstruction unit 22, which ensures that image data X is reconstructed from the measurement data Y, which image data X is then emitted via an image-data interface 23, e.g. displayed on the terminal monitor, stored in the storage medium 16 and/or transmitted to other components within a network via an network interface 13 and a data bus 6.

In this case, the reconstruction unit 22 comprises an initial reconstruction unit 24, which initially generates initial image data $X_0$ on the basis of the measurement data Y using an analytic method. This initial image data $X_0$ is transmitted to an optimization unit 25, within which the image data is thereupon optimized within the scope of an iterative method, as will still be explained below. The optimization unit 25 obtains, inter alia, various reconstruction parameters, e.g. the target function to be used, the regularization terms and/or the weighting factors, as will still be explained below.

It is not necessary for the central control unit 10, as illustrated here, to be designed as an integral unit; rather, it may also be formed from many separate units that are interconnected in a suitable fashion. A multiplicity of the components may also be implemented in software form on suitable microcontrollers. This particularly holds true for the reconstruction unit 22, or the submodules thereof, the initial reconstruction unit 24 and the optimization unit 25. They may be implemented on one or more computer units (e.g. microcontrollers) that are part of the control unit 10, possibly together with further components.

As already explained at the outset, such a reconstruction apparatus according to the invention may also exist outside of such a central actuation unit for actuating the scanner. In this case, the measurement data Y is for example transmitted directly to the image-reconstruction apparatus via a network. More particularly, the image-reconstruction apparatus may be part of the terminal 5, provided the latter has sufficient computational capacity.

Reference is also made to the fact that the central control apparatus 10 and the scanner may have a multiplicity of additional components which are generally found in a magnetic resonance system, or in a CT, PET or SPECT system. However, all these components and the functional principle of such imaging systems are known to a person skilled in the art and therefore need not be described in any more detail in the following text.

The following first of all explains the mathematical basis for carrying out the iterative reconstructions running in the reconstruction unit 22 or the optimization unit 25:

As explained above, an initial reconstruction unit 24 first of all reconstructs initial image data $X_0$ from the measurement data Y with the aid of an analytic method, for example by using a filtered back projection in the case of CT data or, as in the present exemplary embodiment, by using a two-dimensional inverse Fourier transform in the case of MR measurement data.

This data is then input into the iterative optimization method. During the iteration, the image data $X_k$ is updated in each iteration stage k=0, 1, 2, .... This can be described by the equation (3), which was already mentioned above.

As likewise outlined above (cf. equation (5)), the image correction data $\Delta X_k$ in each case is a function of the target function, for example the gradient of the target function multiplied by a relaxation parameter α. This target function $f_z$ should be minimized during the optimization, which is described above in an example by means of equation (7).

If there is an optimization according to an embodiment of the invention utilizing a noise regularization term and an additional, separate sparsity regularization term, this may in general be written in the following statistical fashion:

Thus, in this case, the target function $f_z$ is represented in the following form:

$$f_z = \{L(A \cdot X, Y) + \beta_1 \cdot R(X) + \beta_2 \cdot \|\Psi(X)\|_1\} \quad (8)$$

This target function may, as illustrated above in conjunction with equations (6) and (7), be minimized within the scope of the optimization method according to an embodiment of the invention. The term $L(A \cdot X, Y)$ is a statistically weighted data mismatch term. It matches the error deviation in accordance with the plausibility thereof to the measurement data, i.e. this takes account of how noisy each real measurement data value is. The data deviation term $L(A \cdot X, Y)$, which contains a statistical noise model, may be expressed as a nonnegative logarithmic probability in a form dependent on the suitable mathematical noise model.

Gaussian noise is a suitable noise model for a magnetic resonance imaging system. In this case, the data mismatch term L may be represented as follows:

$$L(A \cdot X, Y) = \|A \cdot X - Y\|_2. \quad (9)$$

This corresponds to the target function as per equation (6), except for that in that case use was not made of either a noise regularization term or a sparsity regularization term. As an alternative to the $L_2$ norm in equation (9), there may also be situations in magnetic resonance imaging scanners, for example during parallel imaging, in which it is better to use a weighted "least-square" form for the target function instead of the $L_2$ norm in order to be able to model the noise statistics in an improved fashion by taking into account the sensitivity profiles of the reception coils.

If the measurement data is CT, PET or SPECT measurement data, a mathematical model that describes Poisson noise should for example be selected. In this case, L can be written as follows:

$$L(A \cdot X, Y) = (Y - A \cdot X)^T W (Y - A \cdot X). \quad (10)$$

Here, W is the convolution kernel, which describes the convolution of the projection data. However, W may also be considered a weighting coefficient, which in this case reflects the fact that Poisson noise depends on the signal amplitude.

The term R(X) in equation (8) is the noise regularization term. It is used to suppress undesired image characteristics such as roughness or noise, for example. Very different terms can be used for R(X), including quadratic functions that minimize the noise, but sadly also reduce the spatial resolution. A specific non-quadratic form is the often used edge-maintaining regularization as per:

$$R(X) = \sum_{j=2}^{N} \frac{1}{2} \phi(x_j - x_{j-1}). \quad (11)$$

Here, $$\phi(t) = \sqrt{1 + (t/\delta)^2} \quad (12)$$

is a potential function, which has been selected such that it increases less quickly than a parabola. The value of δ is a parameter that can be selected freely and determines the full-width at half maximum (FWHM) of the curve. The values $x_j$ are the individual pixels or voxels of the image data matrix X (depending on whether this is two-dimensional or three-dimensional image data) and N is the total number of pixels/voxels in the image. By way of example, this method is described in Jeffrey A. Fessler, Statistical Methods for Image Reconstruction (see citation above).

The parameter or weighting factor $\beta_1$ controls the regularization strength in respect of the noise regularization term R(X), and hence also controls the balance between noise and spatial resolution.

The sparsity correction term $\|\Psi Y(X)\|_1$ in equation (8) serves to maximize the image sparsity by minimizing the $L_1$-norm of the "sparsity transformed" $\Psi(X)$. Different functions may be selected as sparsity transformed $\Psi(X)$. In this case, this particularly preferably is a function with a discrete cosine transform (DCT), with wavelets, with curvelets, finite differences and a gradient operator. It is particularly preferable if the total variation TV(X) of the image X as per $$TV(X) = \sum_{m,n,k} \sqrt{(x_{m+1,n,k} - x_{m,n,k})^2 + (x_{m,n+1,k} - x_{m,n,k})^2 + (x_{m,n,k+1} - x_{m,n,k})^2} \quad (13)$$

can be utilized as sparsity transformed $\Psi(X)$. Here, m, n, k are the positions of the pixels or voxels in one spatial dimension of a three-dimensional Cartesian coordinate system. The variation as per equation (13) corresponds to the vectorial spacing of the image values or intensities between two adjacent pixels or voxels in each spatial direction. By way of example, if an image is only uniformly gray, the total variation TV(X)=0. Another extreme example would be an image with a checkerboard distribution of voxels—alternately white and black. In this case, there would be a maximum in the total variation TV(X).

Using both regularization terms as per equation (8) within the target function surprisingly brings about, in a synergistic fashion, that it is firstly possible to reconstruct undersampled data using an optimized compressed sensing reconstruction method and, secondly, nevertheless possible to reduce the image noise whilst maintaining the image contrast to the best possible extent.

The individual regularization terms R(X) and $\|\Psi(X)\|_1$ are preferably, as illustrated in equation (10), formed as a linear combination by summation using two separate weighting factors $\beta_1$, $\beta_2$. This type of combination guarantees a convex form of the target function, provided that the individual regularization terms R(X) and $\|\Psi(X)\|_1$, and both the data deviation term L(A·X,Y) and the boundary conditions, are also convex, as a result of which the convergence of the iterative optimization process to an unambiguous minimum can also be ensured (cf. Stephen Boyd and Lieven Vandenberghe, Book on Convex Optimization, Cambridge University Press, 2004).

In the process, the noise regularization term R(X) may be selected freely in order to obtain the best noise reduction with simultaneous edge maintenance, whereas the sparsity transformed $\Psi(X)$ may be selected independently thereof in order to obtain maximum undersampling, which in turn may depend on pre-known information relating to the necessary image diversity, for example on the basis of information relating to the region or the organ to be imaged.

As mentioned previously, the weighting factor $\beta_1$ may control the magnitude of the noise regularization, whereas the weighting factor $\beta_2$ independently thereof controls the degree of acceptable undersampling. If $\beta_2$=0 is selected, the method corresponds to the known method of noise reduction with edge maintenance, in the case $\beta_1$=0 there is a classical CS reconstruction for optimum undersampling with high sparsity in the image data. The two weighting factors $\beta_1$, $\beta_2$ are preferably selected such that 0<$\beta_1$+$\beta_2$<1 holds true in order to avoid over-regularization, which would overall slow the iterative process down by too much. By way of example, the summation value $\beta\beta_1$+$\beta_2$ could lie approximately between 0.5 and 0.7.

In an example embodiment, the weighting factors are selected as per $\beta_1$=$\beta\cdot\lambda$ and $\beta_2$=$\beta\cdot(1-\lambda)$, where $\beta$ is the above-mentioned summation value and $\lambda$ is an undersampling rate such that $\lambda$=1 is complete sampling at the Nyquist limit and $\lambda$=0.5 represents a value of 50% undersampling relative to the Nyquist limit. By way of example, this makes it possible automatically to make the component of the sparsity forcing within the optimization method dependent on the actual undersampling rate. However, the user can also likewise set a reconstruction method utilizing an SER by a suitable selection of the weighting factors $\beta_1$, $\beta_2$ and/or the values $\mu$ or $\lambda$, independently of whether undersampled data is in fact present. In this case, the application of an SER method would increase a reduction in reconstruction artifacts such as image details that occur as a result of inconsistencies in the input data (e.g. by X-ray scattering around metal objects in CT recordings or movement artifacts in MR recordings).

In the process, the user of the system may—preferably interactively—determine the weighting factors in a particularly simple fashion and successively carry out multiple reconstructions with different weighting factors and observe the results, for example by setting a value of between 0 and 1 for $\lambda$ by using a mouse pointer on a virtual scale on a graphical user interface. The user can thus navigate at will, in a step-less fashion, between reconstructed images, which are fully noise-constricted in one extreme case and which are fully sparsity-constricted in the other extreme case, in order thus to clarify specific aspects in the region of interest.

Incidentally, the boundary condition that no negative image data may be produced (i.e. X>0) may also be complemented during the optimization by further boundary conditions, such as e.g. upper limits for the image values, beam-hardening boundary conditions, boundary conditions on the basis of previous images, etc.

Figure 2:
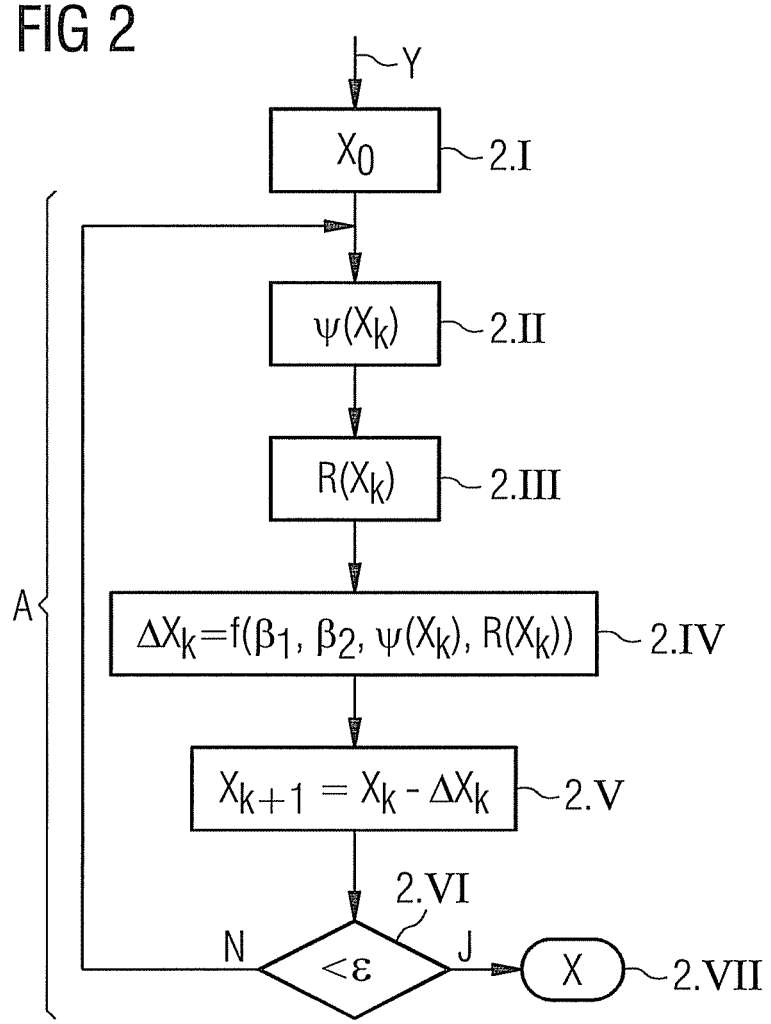
FIG. 2 shows a flowchart for a possible procedure of a iterative reconstruction method according to the invention as per a first example embodiment.

FIG. 2 shows a flowchart for the progression of the optimization method as per a particularly preferred method, wherein there is one single-stage update of the image in one iteration step.

The method starts with the acquisition of measurement data Y, which is initially used in the step 2.I to generate initial image data, for example by way of a classical analytic method (e.g. using a two-dimensional inverse Fourier transform in the case of raw MR data). This initial image data $X_0$, estimated thus, is then improved in the subsequent iterative optimization process, wherein an iteration stage A is generally run through a number of times.

To this end, the sparsity transformed $\Psi(X_k)$ for the current initial image data $X_0$ is firstly calculated in a step 2.II. By way of example, this may be performed with the aid of equation (13) if the total variation TV(X) is used as sparsity transformed $\Psi(X)$.

In a further step 2.III, the noise regularization term $R(X_k)$ is then calculated for the current image data, i.e. for the initial image data $X_0$ here in the first iteration step; this may be carried out, for example, using equations (11) and (12).

The image correction data $\Delta X_k$ is then subsequently calculated in step 2.IV, for example according to equation (5) in conjunction with equation (8). Since the image correction data $\Delta X_k$ therefore is a function of the sparsity regularization term $\|\Psi(X)\|_1$ (or the sparsity transformed $\Psi(X_k)$), the noise regularization term $R(X_k)$ and the associated weighting factors $\beta_1$ and $\beta_2$, this calculation has been illustrated in a simplified fashion in FIG. 2 as a function $f(\beta_1, \beta_2, \Psi(X_k), R(X_k))$. However, this does not mean that the image correction data $\Delta X_k$ does not also depend on other parameters or functions, for example on the statistically weighted data mismatch term L(A·X,Y) as per equation (9) or (10), i.e. $f(Y, X_k, \beta_1, \beta_2, \Psi(X_k), R(X_k))$.

The image data then is updated in step 2.V by subtracting the calculated image correction data $\Delta X_k$ as per equation (3) from the current image data $X_k$ (from the initial image data $X_0$ in the first iteration step).

Then, a convergence criterion is checked in a subsequent step 2.VI, for example to see whether the target function or the image correction data lies under a prescribed ε-value. Should this not be the case (branch N), there is a new iteration step with the updated image data $X_{k+1}$ as input data. Otherwise (branch Y), the reconstruction method is completed in step 2.VII and the current image data is accepted as final image data X.

Figure 3:
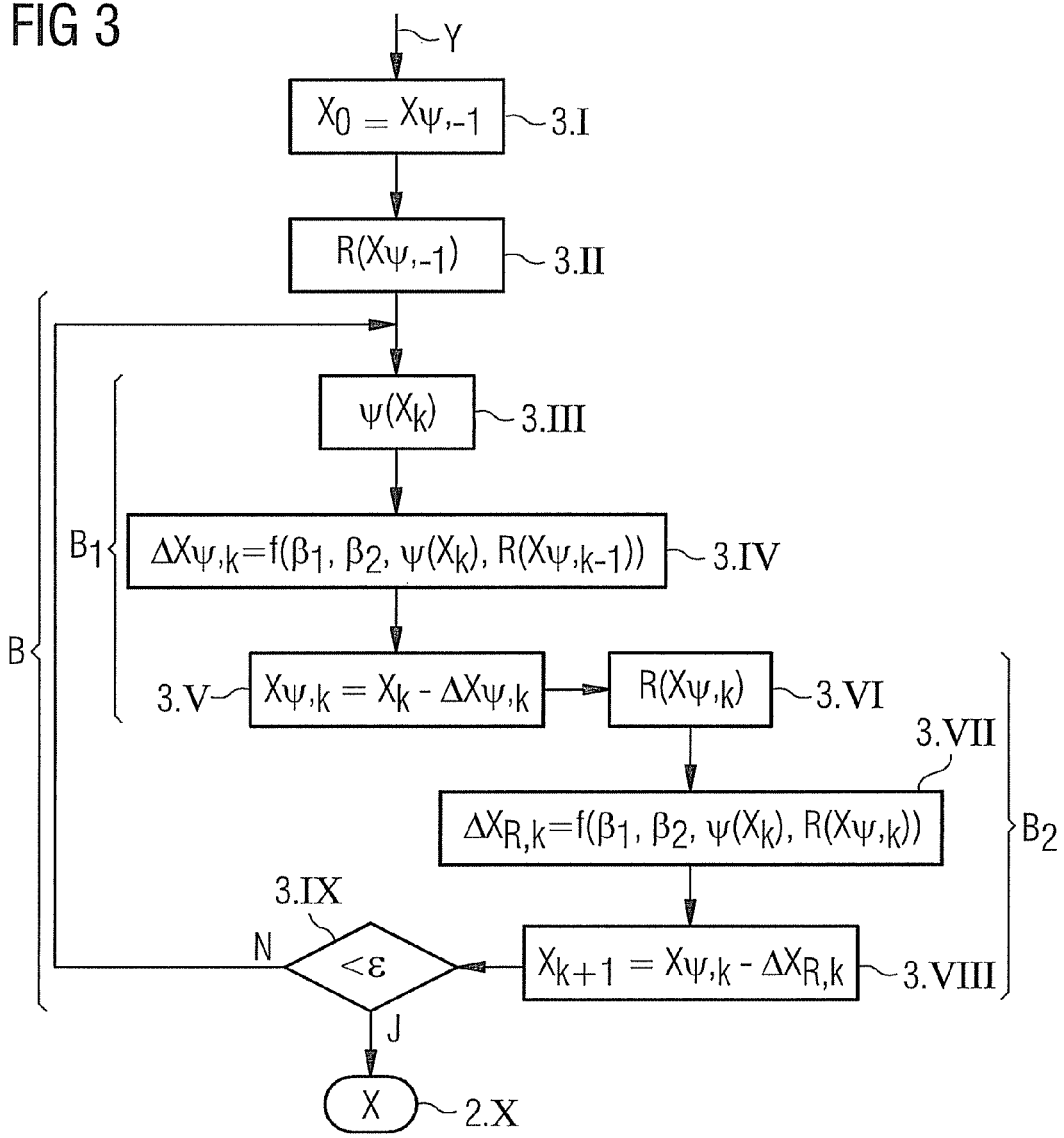
FIG. 3 shows a flowchart for a possible procedure of an iterative reconstruction method according to the invention as per a second example embodiment.

FIG. 3 shows a slightly modified method, in which the image updating in respect of the sparsity regularization term $\|\Psi(X)\|_1$ and in respect of the noise regularization term $R(X_k)$ is successively carried out in two partial stages $B_1$ and $B_2$; i.e. in this case an iteration step B consists of two partial stages $B_1$ and $B_2$.

In step 3.I, (as in the step 2.I according to the method as per FIG. 2), the method first of all starts off with reconstructing initial image data $X_0$ from the measurement data Y. That is to say, the initial image data $X_0$ is estimated using a simple reconstruction method.

Then—unlike the method variant according to FIG. 2—a first noise regularization term $R(X_{\Psi,-1})$ is calculated in step 3.II before the iteration loop, wherein, as illustrated in step 3.I, the image data $X_{\Psi,-1}$ is equated to the initial image data $X_0$.

Only then does the first partial stage $B_1$ of the iteration loop start in step 3.III by calculating the sparsity transformed $\Psi(X_k)$ for the current initial image data $X_k$ (i.e. first of all with the initial image data $X_0$), wherein this step is again formed in an analog fashion to step 2.II in the method as per FIG. 2.

Subsequently, first image correction data $\Delta X_{\Psi,k}$ is established in step 3.IV. Here, in principle, the same function is utilized as in step 2.IV as per the method variant according to FIG. 2, but with the difference that, in order to calculate the first image correction data $\Delta X_{\Psi,k}$, it is only the current sparsity regularization term $\|\Psi(X)\|_1$, as calculated in step 3.III, that is used, but use is made of the noise regularization term $R(X_{\Psi,k-1})$ from the preceding iteration step. In the case of the first iteration step, this is the noise regularization term $R(X_{\Psi,-1})$ calculated specifically in step 3.II before the start of the iteration.

Analogously to step 2.V, the image data is then updated in step 3.V, wherein, however, current interim image data $X_{\Psi,k}$ is established in this case, which is then once again updated in respect of the noise regularization term within the second partial stage $B_2$ of the iteration step B. To this end, the current noise regularization term $R(X_{\Psi,k})$ is firstly calculated in step 3.VI on the basis of the current interim image data $X_{\Psi,k}$.

Then, second image correction data $\Delta X_{R,k}$ is thereupon calculated in step 3.VII, wherein, in this case too, the same function is used as in step 2.IV, but now use is made of the sparsity transformed $\Psi(X_k)$, already calculated in the first stage $B_1$ in step 3.III, and the current noise regularization term $R(X_{\Psi,k})$ calculated in the second stage $B_2$ in step 3.VI.

Finally, in step 3.VIII, there is an update of the current interim image data $X_{\Psi,k}$ utilizing the second image correction data $\Delta X_{R,k}$ established in step 3.VII.

Analogously to step 2.VI, a check is then carried out in step 3.IX as to whether the target function and/or the image correction data (possibly in each case also the two individual image correction data $\Delta X_{\Psi,k}$ and $\Delta X_{R,k}$) lie(s) below a prescribed ε-value. Should this not be the case (branch N), the next iteration step is run through, wherein the running variable k is incremented by 1. If the convergence criterion is satisfied (branch Y), the optimization method is completed in step 3.X and the current image data is accepted as final image data X.

The method and construction apparatus were mainly explained on the basis of a reconstruction of medical image data. However, the invention is not restricted to an application in the medical field, but in principle magnetic resonance imaging, computed tomography, PET or SPECT images, etc., for different purpose, e.g. for materials testing or the like, may also be generated and processed.

Finally, reference is once again made to the fact that the above-described methods and devices are merely preferred example embodiments of the invention, and that the invention may be varied by a person skilled in the art without departing from the scope of the invention as prescribed by the claims. For completeness' sake, reference is also made to the fact that the use of the indefinite article "a" or "an" does not preclude the relevant features from being able to be present a number of times. Likewise, the term "unit" or "module" does not preclude these from consisting of a plurality of components, which may possibly also be distributed in space.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data based upon measurement data from an imaging system, the method comprising:
    determining initial image data based on the measurement data; and
    reconstructing the image data by optimizing the initial image data, in an iterative optimization method, based on at least an edge-maintaining noise regularization term and a sparsity regularization term, the edge-maintaining noise regularization term and the sparsity regularization term being independent of one another.

2. The method as claimed in claim 1, wherein during each iteration of the iterative optimization method, the optimizing the initial image data includes,
    determining current image correction data based on the edge-maintaining noise regularization term and the sparsity regularization term,
    optimizing the initial image data based on previously optimized image data and the current image correction data, and
    determining whether to proceed to a next iteration of the iterative optimization method or to terminate the iterative optimization method based on the optimized initial image data and a convergence threshold.

3. The method as claimed in claim 1, wherein the edge-maintaining noise regularization term and the sparsity regularization term form a target function to be optimized during each iteration of the iterative optimization method.

4. The method as claimed in claim 3, wherein the target function and at least one boundary condition associated with the target function are convex functions.

5. The method as claimed in claim 1, wherein the edge-maintaining noise regularization term and the sparsity regularization term are respectively weighted by a weighting factor during the optimizing.

6. The method as claimed in claim 5, wherein the weighting factor of the edge-maintaining noise regularization term and the weighting factor of the sparsity regularization term are selected such that a sum of the two weighting factors is between 0 and 1.

7. The method as claimed in claim 1, wherein the measurement data is sampled at a rate below a Nyquist limit.

8. The method as claimed in claim 5, wherein the weighting factors are selected by a user.

9. The method as claimed in claim 5, wherein the weighting factor of the sparsity regularization term is selected as a function of a sampling rate at which the measurement data are sampled.

10. The method as claimed in claim 9, wherein in a sum of the weighting factor of the edge-maintaining noise regularization term and the weighting factor of the sparsity regularization term, the weighting factor of the sparsity regularization term is selected as a function of the sampling rate.

11. The method as claimed in claim 2, wherein each iteration of the iterative optimization method includes a first stage and a second stage,
    in the first stage, the determining the current image correction data includes,
        determining the sparsity regularization term, and
        determining sparsity based current image correction data based on at least the determined sparsity regularization term and an edge-maintaining noise regularization term corresponding to a previous iteration, wherein
        the optimizing the initial image data first optimizes the initial image data based on the previously optimized image data and the sparsity based current image correction data, and
    in the second stage, the determining the corresponding current image correction data includes,
        determining the edge-maintaining noise regularization term based on the first optimized initial image data, and
        determining noise based image correction data based on at least the determined sparsity regularization term and the determined edge-maintaining noise regularization term, wherein
    the optimizing the initial image data second optimizes the initial image data based on the first optimized initial image data and the noise based image correction data.

12. The method as claimed in claim 1, wherein the determining the initial image data determines the initial image data using a medical image acquiring system.

13. An image-reconstruction apparatus for reconstructing image data of an object, comprising:
    a measurement-data interface configured to receive measurement data obtained via an imaging system;
    a reconstruction unit configured to,
        determine initial image data based on the measurement data, and
        reconstruct the image data by optimizing the initial image data, in an iterative optimization method, based on at least an edge-maintaining noise regularization term and a sparsity regularization term, the edge-maintaining noise regularization term and the sparsity regularization term being independent of one another; and an image-data interface configured to output the reconstructed image data.

14. A non-transitory computer readable medium including a computer program product, the computer program product comprising computer instructions, which when executed by a processor, causes the processor to perform the method as claimed in claim 1.

15. The method as claimed in claim 2, wherein the edge-maintaining noise regularization term and the sparsity regularization term form a target function to be optimized during each iteration of the iterative optimization method.

16. The method as claimed in claim 15, wherein the target function and at least one boundary condition associated with the target function are convex functions.

17. The method as claimed in claim 6, wherein the weighting factors are selected by a user.

18. The method as claimed in claim 6, wherein the weighting factor of the sparsity regularization term is selected as a function of a sampling rate at which the measurement data are sampled.

19. The method as claimed in claim 7, wherein the weighting factors are selected by a user.

20. The method as claimed in claim 7, wherein the weighting factor of the sparsity regularization term is selected as a function of a sampling rate at which the measurement data are sampled.

21. The method as claimed in claim 19, wherein in a sum of the weighting factor of the edge-maintaining noise regularization term and the weighting factor of the sparsity regularization term, the weighting factor of the sparsity regularization term is selected as a function of the sampling rate.

22. The method as claimed in claim 20, wherein in a sum of the weighting factor of the edge-maintaining noise regularization term and the weighting factor of the sparsity regularization term, the weighting factor of the sparsity regularization term is selected as a function of the sampling rate.

23. The method as claimed in claim 2, wherein the determining whether to proceed to the next iteration of the iterative optimization method includes,
   comparing the current image correction data to the convergence threshold, and
   proceeding to the next iteration if the current image correction data is less than the convergence threshold.

* * * * *